US008568467B2

(12) United States Patent
Dorn et al.

(10) Patent No.: US 8,568,467 B2
(45) Date of Patent: Oct. 29, 2013

(54) TRANS-LUMINAL SURGICAL DEVICE (75) Inventors: Jurgen Dorn, Neulussheim (DE);
Martin Wuebbeling, Mannheim (DE);
Beate Walter, Stutensee (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 1085 days.

(21) Appl. No.: 10/541,875

(22) PCT Filed: Jan. 15, 2004

(86) PCT No.: PCT/EP2004/000248
§ 371 (c)(1),
(2), (4) Date: Apr. 5, 2006

(87) PCT Pub. No.: WO2004/062458
PCT Pub. Date: Jul. 29, 2004

(65) Prior Publication Data
US 2006/0212105 A1    Sep. 21, 2006

(30) Foreign Application Priority Data

Jan. 15, 2003 (GB) .................................. 0300915.6
Nov. 24, 2003 (GB) .................................. 0327306.7

(51) Int. Cl.
*A61F 2/06* (2013.01)
(52) U.S. Cl.
USPC .......................................... 623/1.12; 606/194
(58) Field of Classification Search
USPC ................ 623/1.11, 1.12; 606/108, 194, 200; 604/523
See application file for complete search history.

(56) References Cited

U.S. PATENT DOCUMENTS

| 3,485,234 A | 12/1969 | Stevens |
| 4,580,568 A | 4/1986 | Gianturco |
| 4,636,346 A | 1/1987 | Gold et al. |
| 4,759,748 A | 7/1988 | Reed |
| 4,768,507 A | 9/1988 | Fischell et al. |
| 4,817,613 A | 4/1989 | Jaraczewski et al. |

(Continued)

FOREIGN PATENT DOCUMENTS

| CA | 2449961 A1 | 1/2003 |
| DE | 19936059 A1 | 2/2001 |

(Continued)

OTHER PUBLICATIONS

Jun. 23, 2009 Examiners Requisition in Canadian application No. 2,513,082 filed on Jan. 15, 2004.

(Continued)

*Primary Examiner* — Kathleen Holwerda
*Assistant Examiner* — Sarah W Aleman
(74) *Attorney, Agent, or Firm* — Rutan & Tucker, LLP (57) ABSTRACT

A device for trans-luminal delivery of a self-expanding stent or other surgical device and which is designed for rapid exchange over a guidewire has a guidewire lumen that adjacent its proximal exit port lies side-by-side with the line of the shaft of the device. A sleeve which surrounds and confines the stent has a proximal end that is shaped around the guidewire exit port to show in profile a shape reminiscent of the nose of a dolphin. In preferred embodiments, the sleeve also has a tapered distal tip that is withdrawn proximally over the length of the stent to release it, progressively, from its distal end. The configuration delivers simplicity of design, enhanced performance and reliability in use.

37 Claims, 6 Drawing Sheets

(56) References Cited

U.S. PATENT DOCUMENTS

| | | | |
|---|---|---|---|
| 4,842,590 A | 6/1989 | Tanabe et al. | |
| 4,950,227 A | 8/1990 | Savin et al. | |
| 4,979,280 A | 12/1990 | Weil | |
| 5,026,377 A | 6/1991 | Burton et al. | |
| 5,061,257 A | 10/1991 | Martinez et al. | |
| 5,085,662 A | 2/1992 | Willard | |
| 5,158,548 A | 10/1992 | Lau et al. | |
| 5,201,757 A | 4/1993 | Heyn et al. | |
| 5,221,372 A | 6/1993 | Olson | |
| 5,234,416 A | 8/1993 | Macaulay et al. | |
| 5,254,107 A | 10/1993 | Soltesz | |
| 5,275,152 A | 1/1994 | Krauter et al. | |
| 5,290,295 A | 3/1994 | Querals et al. | |
| 5,443,477 A | 8/1995 | Marin et al. | |
| 5,445,646 A | 8/1995 | Euteneuer et al. | |
| 5,453,090 A | 9/1995 | Martinez et al. | |
| 5,484,444 A | 1/1996 | Braunschweiler et al. | |
| 5,507,768 A | 4/1996 | Lau et al. | |
| 5,507,769 A | 4/1996 | Marin et al. | |
| 5,522,883 A | 6/1996 | Slater et al. | |
| 5,534,007 A | 7/1996 | St. Germain et al. | |
| 5,571,135 A | 11/1996 | Fraser et al. | |
| 5,571,168 A | 11/1996 | Toro | |
| 5,603,698 A * | 2/1997 | Roberts et al. | 604/104 |
| 5,603,705 A | 2/1997 | Berg | |
| 5,617,900 A | 4/1997 | Weil | |
| 5,618,300 A | 4/1997 | Marin et al. | |
| 5,634,928 A | 6/1997 | Fischell et al. | |
| 5,643,278 A | 7/1997 | Wijay | |
| 5,662,622 A | 9/1997 | Gore et al. | |
| 5,662,703 A | 9/1997 | Yurek et al. | |
| 5,674,208 A | 10/1997 | Berg et al. | |
| 5,683,451 A | 11/1997 | Lenker et al. | |
| 5,690,642 A | 11/1997 | Osborne et al. | |
| 5,690,644 A | 11/1997 | Yurek et al. | |
| 5,700,269 A | 12/1997 | Pinchuk et al. | |
| 5,702,418 A | 12/1997 | Ravenscroft | |
| 5,707,376 A | 1/1998 | Kavteladze et al. | |
| 5,709,703 A | 1/1998 | Lukic et al. | |
| 5,733,267 A | 3/1998 | Del Toro | |
| 5,738,667 A | 4/1998 | Solar | |
| 5,741,327 A | 4/1998 | Frantzen | |
| 5,772,668 A | 6/1998 | Summers et al. | |
| 5,772,669 A | 6/1998 | Vrba | |
| 5,788,707 A | 8/1998 | Del Toro et al. | |
| 5,792,144 A | 8/1998 | Fischell et al. | |
| 5,792,365 A | 8/1998 | Torini et al. | |
| 5,797,952 A | 8/1998 | Klein | |
| 5,811,043 A | 9/1998 | Horrigan et al. | |
| 5,817,101 A | 10/1998 | Fiedler | |
| 5,824,041 A | 10/1998 | Lenker et al. | |
| 5,910,145 A | 6/1999 | Fischell et al. | |
| 5,951,495 A | 9/1999 | Berg et al. | |
| 5,954,651 A | 9/1999 | Berg et al. | |
| 5,957,930 A | 9/1999 | Vrba | |
| 5,968,052 A | 10/1999 | Sullivan, III et al. | |
| 5,980,533 A | 11/1999 | Holman | |
| 5,984,964 A | 11/1999 | Roberts et al. | |
| 5,993,460 A | 11/1999 | Beitelia et al. | |
| 6,019,778 A | 2/2000 | Wilson et al. | |
| 6,039,749 A | 3/2000 | Marin et al. | |
| 6,042,588 A | 3/2000 | Munsinger et al. | |
| 6,042,589 A | 3/2000 | Marianne | |
| 6,077,295 A | 6/2000 | Limon et al. | |
| 6,080,102 A | 6/2000 | Konou et al. | |
| 6,096,045 A | 8/2000 | Del Toro et al. | |
| 6,126,685 A | 10/2000 | Lenker et al. | |
| 6,143,016 A | 11/2000 | Bleam et al. | |
| 6,146,415 A | 11/2000 | Fitz | |
| 6,152,944 A | 11/2000 | Holman et al. | |
| 6,168,610 B1 | 1/2001 | Marin et al. | |
| 6,168,616 B1 | 1/2001 | Brown, III | |
| 6,177,140 B1 | 1/2001 | Patil et al. | |
| 6,190,393 B1 | 2/2001 | Bevier et al. | |
| 6,206,888 B1 | 3/2001 | Bicek et al. | |
| 6,212,422 B1 | 4/2001 | Berg et al. | |
| 6,217,586 B1 | 4/2001 | Mackenzie | |
| 6,221,081 B1 | 4/2001 | Mikus et al. | |
| 6,228,110 B1 | 5/2001 | Munsinger | |
| 6,238,402 B1 | 5/2001 | Sullivan, III et al. | |
| 6,238,410 B1 | 5/2001 | Vrba et al. | |
| 6,238,430 B1 | 5/2001 | Klumb et al. | |
| 6,241,758 B1 | 6/2001 | Cox | |
| 6,254,608 B1 | 7/2001 | Solar | |
| 6,254,609 B1 | 7/2001 | Vrba et al. | |
| 6,254,611 B1 | 7/2001 | Vrba | |
| 6,264,671 B1 | 7/2001 | Stack et al. | |
| 6,293,966 B1 | 9/2001 | Frantzen | |
| 6,296,622 B1 | 10/2001 | Kurz et al. | |
| 6,306,145 B1 | 10/2001 | Leschinsky | |
| 6,331,186 B1 | 12/2001 | Wang et al. | |
| 6,342,066 B1 | 1/2002 | Toro et al. | |
| 6,350,278 B1 | 2/2002 | Lenker et al. | |
| 6,352,553 B1 | 3/2002 | van der Burg et al. | |
| 6,352,561 B1 | 3/2002 | Leopold et al. | |
| 6,355,060 B1 | 3/2002 | Lenker et al. | |
| 6,361,555 B1 | 3/2002 | Wilson | |
| 6,368,344 B1 | 4/2002 | Fitz | |
| 6,371,979 B1 | 4/2002 | Beyar et al. | |
| 6,375,676 B1 | 4/2002 | Cox | |
| 6,379,365 B1 | 4/2002 | Diaz | |
| 6,380,457 B1 | 4/2002 | Yurek et al. | |
| 6,387,118 B1 | 5/2002 | Hanson | |
| 6,391,050 B1 | 5/2002 | Broome | |
| 6,391,051 B2 * | 5/2002 | Sullivan et al. | 623/1.12 |
| 6,402,760 B1 | 6/2002 | Fedida | |
| 6,413,269 B1 | 7/2002 | Bui et al. | |
| 6,425,898 B1 | 7/2002 | Wilson et al. | |
| 6,432,129 B2 | 8/2002 | DiCaprio | |
| 6,443,979 B1 | 9/2002 | Stalker et al. | |
| 6,468,298 B1 | 10/2002 | Pelton | |
| 6,482,211 B1 | 11/2002 | Choi | |
| 6,488,694 B1 | 12/2002 | Lau et al. | |
| 6,505,066 B2 | 1/2003 | Berg et al. | |
| 6,514,196 B1 | 2/2003 | Sullivan et al. | |
| 6,514,280 B1 | 2/2003 | Gilson | |
| 6,517,547 B1 | 2/2003 | Feeser et al. | |
| 6,517,569 B2 | 2/2003 | Mikus et al. | |
| 6,520,983 B1 | 2/2003 | Colgan et al. | |
| 6,530,947 B1 | 3/2003 | Euteneuer et al. | |
| 6,554,841 B1 | 4/2003 | Yang | |
| 6,572,643 B1 | 6/2003 | Gharibadeh | |
| 6,576,002 B2 | 6/2003 | Dobak, III | |
| 6,579,297 B2 | 6/2003 | Bicek et al. | |
| 6,582,460 B1 | 6/2003 | Cryer | |
| 6,592,569 B2 | 7/2003 | Bigus et al. | |
| 6,599,296 B1 | 7/2003 | Gillick et al. | |
| 6,605,109 B2 | 8/2003 | Fiedler | |
| 6,613,075 B1 | 9/2003 | Healy et al. | |
| 6,616,681 B2 | 9/2003 | Hanson et al. | |
| 6,626,934 B2 | 9/2003 | Blaeser et al. | |
| 6,629,981 B2 | 10/2003 | Bui et al. | |
| 6,629,992 B2 | 10/2003 | Bigus et al. | |
| 6,641,606 B2 | 11/2003 | Ouriel et al. | |
| 6,656,212 B2 | 12/2003 | Ravenscroft et al. | |
| 6,656,213 B2 | 12/2003 | Solem | |
| 6,660,031 B2 | 12/2003 | Tran et al. | |
| 6,663,614 B1 * | 12/2003 | Carter | 604/525 |
| 6,663,666 B1 | 12/2003 | Quiachon et al. | |
| 6,676,666 B2 | 1/2004 | Vrba et al. | |
| 6,676,693 B1 | 1/2004 | Belding et al. | |
| 6,689,120 B1 | 2/2004 | Gerdts | |
| 6,695,812 B2 * | 2/2004 | Estrada et al. | 604/103.09 |
| 6,695,862 B2 | 2/2004 | Cox et al. | |
| 6,699,274 B2 | 3/2004 | Stinson | |
| 6,702,843 B1 | 3/2004 | Brown et al. | |
| 6,726,712 B2 | 4/2004 | Raeder-Devens et al. | |
| 6,726,714 B2 | 4/2004 | DiCaprio et al. | |
| 6,736,839 B2 | 5/2004 | Cummings | |
| 6,743,219 B1 | 6/2004 | Dwyer et al. | |
| 6,749,627 B2 | 6/2004 | Thompson et al. | |
| 6,773,446 B2 | 8/2004 | Dwyer et al. | |
| 6,780,174 B2 | 8/2004 | Solar et al. | |
| 6,786,918 B1 | 9/2004 | Krivoruchko et al. | |

(56) References Cited

U.S. PATENT DOCUMENTS

| | | |
|---|---|---|
| 6,790,221 B2 | 9/2004 | Monroe et al. |
| 6,827,731 B2 | 12/2004 | Armstrong et al. |
| 6,830,575 B2 | 12/2004 | Stenzel et al. |
| 6,843,802 B1 | 1/2005 | Villalobos et al. |
| 6,849,084 B2 | 2/2005 | Rabkin et al. |
| 6,858,034 B1 | 2/2005 | Hijlkema et al. |
| 6,860,898 B2 | 3/2005 | Stack et al. |
| 6,866,669 B2 | 3/2005 | Buzzard et al. |
| 6,884,259 B2 | 4/2005 | Tran et al. |
| 6,899,727 B2 | 5/2005 | Armstrong et al. |
| 6,926,732 B2 | 8/2005 | Derus et al. |
| 6,939,352 B2 | 9/2005 | Buzzard et al. |
| 6,942,688 B2 | 9/2005 | Bartholf et al. |
| 6,945,989 B1 * | 9/2005 | Betelia et al. ............ 623/1.11 |
| 7,001,423 B2 | 2/2006 | Euteneuer et al. |
| 7,025,773 B2 | 4/2006 | Gittings et al. |
| 7,052,511 B2 | 5/2006 | Weldon et al. |
| 7,074,236 B2 | 7/2006 | Rabkin et al. |
| 7,147,657 B2 | 12/2006 | Chiang et al. |
| 7,163,552 B2 | 1/2007 | Diaz |
| 7,172,617 B2 | 2/2007 | Colgan et al. |
| 7,198,636 B2 | 4/2007 | Cully et al. |
| 7,238,197 B2 * | 7/2007 | Sequin et al. ............ 623/1.11 |
| 7,297,302 B2 | 11/2007 | Berg et al. |
| 7,550,001 B2 | 6/2009 | Dorn et al. |
| 8,025,692 B2 | 9/2011 | Feeser |
| 8,043,364 B2 | 10/2011 | Lombardi et al. |
| 2001/0034549 A1 | 10/2001 | Bartholf et al. |
| 2002/0016597 A1 | 2/2002 | Dwyer et al. |
| 2002/0077691 A1 | 6/2002 | Nachtigall |
| 2002/0183826 A1 | 12/2002 | Dorn et al. |
| 2003/0050686 A1 | 3/2003 | Raeder-Devens et al. |
| 2003/0093106 A1 | 5/2003 | Brady et al. |
| 2003/0109886 A1 * | 6/2003 | Keegan et al. ............ 606/108 |
| 2004/0006380 A1 | 1/2004 | Buck et al. |
| 2004/0015228 A1 | 1/2004 | Lombardi et al. |
| 2004/0073291 A1 | 4/2004 | Brown et al. |
| 2004/0127912 A1 | 7/2004 | Rabkin et al. |
| 2004/0148009 A1 | 7/2004 | Buzzard et al. |
| 2004/0153137 A1 | 8/2004 | Gaschino et al. |
| 2004/0181239 A1 | 9/2004 | Dorn et al. |
| 2004/0186547 A1 | 9/2004 | Dorn et al. |
| 2004/0193180 A1 | 9/2004 | Buzzard et al. |
| 2004/0199240 A1 | 10/2004 | Dorn |
| 2004/0215229 A1 | 10/2004 | Coyle |
| 2004/0215317 A1 | 10/2004 | Cummings |
| 2004/0254637 A1 | 12/2004 | Yang et al. |
| 2005/0004515 A1 | 1/2005 | Hart et al. |
| 2005/0021123 A1 | 1/2005 | Dorn et al. |
| 2005/0027345 A1 | 2/2005 | Horan et al. |
| 2005/0038493 A1 | 2/2005 | Feeser |
| 2005/0065590 A1 | 3/2005 | Shelso |
| 2005/0065591 A1 | 3/2005 | Moberg et al. |
| 2005/0080476 A1 | 4/2005 | Gunderson et al. |
| 2005/0090890 A1 | 4/2005 | Wu et al. |
| 2005/0149159 A1 | 7/2005 | Andreas et al. |
| 2005/0165352 A1 | 7/2005 | Henry et al. |
| 2005/0209670 A1 | 9/2005 | George et al. |
| 2005/0209672 A1 | 9/2005 | George et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2006/0015171 A1 | 1/2006 | Armstrong |
| 2006/0030923 A1 | 2/2006 | Gunderson |
| 2006/0074477 A1 | 4/2006 | Berthiaume et al. |
| 2006/0085057 A1 | 4/2006 | George et al. |
| 2006/0100686 A1 | 5/2006 | Bolduc et al. |
| 2006/0212105 A1 | 9/2006 | Dorn et al. |
| 2006/0259124 A1 | 11/2006 | Matsuoka et al. |
| 2006/0282152 A1 | 12/2006 | Beyerlein et al. |
| 2007/0055338 A1 | 3/2007 | Dorn |
| 2007/0055339 A1 | 3/2007 | George et al. |
| 2007/0055340 A1 | 3/2007 | Pryor |
| 2007/0055342 A1 | 3/2007 | Wu et al. |
| 2007/0060943 A1 | 3/2007 | Dorn et al. |
| 2007/0060999 A1 | 3/2007 | Randall et al. |
| 2007/0073379 A1 | 3/2007 | Chang |
| 2007/0083256 A1 | 4/2007 | Dorn |
| 2007/0100420 A1 | 5/2007 | Kavanagh et al. |
| 2007/0100422 A1 | 5/2007 | Shumer et al. |
| 2007/0118201 A1 | 5/2007 | Pappas et al. |
| 2007/0118206 A1 | 5/2007 | Colgan et al. |
| 2007/0179519 A1 | 8/2007 | Huisun |
| 2007/0191864 A1 | 8/2007 | Shumer |
| 2007/0191865 A1 | 8/2007 | Pappas |
| 2007/0191925 A1 | 8/2007 | Dorn |
| 2007/0219624 A1 | 9/2007 | Brown et al. |
| 2008/0262506 A1 * | 10/2008 | Griffin et al. ............ 606/108 |
| 2010/0179637 A1 | 7/2010 | Dorn et al. |

FOREIGN PATENT DOCUMENTS

| | | |
|---|---|---|
| DE | 10201151 A1 | 7/2003 |
| EP | 0221570 A2 | 5/1987 |
| EP | 380873 A2 | 8/1990 |
| EP | 0380873 A2 | 8/1990 |
| EP | 0436303 A1 | 7/1991 |
| EP | 505686 A1 | 9/1992 |
| EP | 0564894 A1 | 10/1993 |
| EP | 611556 A1 | 8/1994 |
| EP | 0611556 A1 | 8/1994 |
| EP | 0630657 A1 | 12/1994 |
| EP | 0699451 A2 | 3/1996 |
| EP | 941716 A2 | 9/1999 |
| EP | 1084728 A1 | 3/2001 |
| EP | 1095634 A2 | 5/2001 |
| EP | 1488763 A2 | 12/2004 |
| GB | 0114939 A | 4/1918 |
| JP | 1150516 A | 6/1989 |
| JP | 3725550 | 5/1999 |
| JP | 11505162 | 5/1999 |
| JP | 11313893 A | 11/1999 |
| JP | 2004530507 T | 10/2004 |
| WO | WO-9636298 A1 | 11/1996 |
| WO | WO-9639998 A2 | 12/1996 |
| WO | WO-9707756 A1 | 3/1997 |
| WO | WO-9812988 A1 | 4/1998 |
| WO | WO-9814224 A2 | 4/1998 |
| WO | WO-9925280 A1 | 5/1999 |
| WO | WO-9944541 A1 | 9/1999 |
| WO | WO-9947075 A1 | 9/1999 |
| WO | WO-9951167 A2 | 10/1999 |
| WO | WO-0000104 A1 | 1/2000 |
| WO | WO-0071059 A1 | 11/2000 |
| WO | WO-0078248 A1 | 12/2000 |
| WO | WO-0117458 A1 | 3/2001 |
| WO | 0134061 A1 | 5/2001 |
| WO | WO-0134061 A1 | 5/2001 |
| WO | WO-0164134 A1 | 9/2001 |
| WO | WO-0215820 A2 | 2/2002 |
| WO | WO-02087470 A1 | 11/2002 |
| WO | WO-02102279 A2 | 12/2002 |
| WO | WO 03/003944 A2 | 1/2003 |
| WO | WO-03002019 A2 | 1/2003 |
| WO | WO-03002020 A2 | 1/2003 |
| WO | WO-03003944 A2 | 1/2003 |
| WO | 2003030783 A1 | 4/2003 |
| WO | WO-2004062458 A2 | 7/2004 |
| WO | 2005053574 A2 | 6/2005 |

OTHER PUBLICATIONS

Oct. 7, 2005 International Search Report in international application No. PCT/EP2004/013339 filed on Nov. 24, 2004.

Oct. 7, 2005 Written Opinion of the ISA in international application No. PCT/EP2004/013339 filed on Nov. 24, 2004.

Apr. 1, 2007 International Preliminary Report on Patentability in international application No. PCT/EP2004/013339 filed on Nov. 24, 2004.

Jan. 24, 2003 International Search Report in international application No. PCT/EP2002/11082 filed on Oct. 2, 2002.

Jan. 7, 2004 International Preliminary Report on Patentability in international application No. PCT/EP02/11082 filed on Oct. 2, 2002.

(56) References Cited

OTHER PUBLICATIONS

Jan. 23, 2003 International Search Report in international application No. PCT/EP02/07435 filed on Jul. 4, 2002.
Jan. 20, 2003 International Preliminary Report on Patentability in international application No. PCT/EP02/07435 filed on Jul. 4, 2002.
Mar. 30, 2009 Non-Final Office Action in U.S. Appl. No. 10/580,200, filed on Mar. 30, 2007.
Nov. 9, 2009 Final Office Action in U.S. Appl. No. 10/580,200, filed on Mar. 30, 2007.
Mar. 10, 2008 Non-Final Office Action in U.S. Appl. No. 10/490,752, filed on Jul. 21, 2004.
Dec. 23, 2009 Final Office Action in U.S. Appl. No. 10/490,752, filed on Jul. 21, 2004.
Aug. 18, 2008 Non-Final Office Action in U.S. patent application No. 10/483,020 filed on Mar. 31, 2004.
Feb. 3, 2009 Final Office Action in U.S. Appl. No. 10/483,020, filed on Mar. 31, 2004.
Jul. 21, 2009 Non-Final Office Action in U.S. Appl. No. 10/483,020, filed on Mar. 31, 2004.
Oct. 26, 2009 Japanese Office action in Japanese patent application No. 2006-500573.
Nov. 22, 2004 International Search Report in international application No. PCT/EP2004/000248 filed on Jan. 15, 2004.
Nov. 11, 2004 Written Opinion of the ISA in international application No. PCT/EP2004/000248 filed on Jan. 15, 2004.
Jul. 15, 2005 International Preliminary Report on Patentability in international application No. PCT/EP2004/000248 filed on Jan. 15, 2004.
Feb. 4, 2008 International Search Report in international application No. PCT/EP20071063347 filed on Dec. 5, 2007.
Jun. 10, 2009 International Preliminary Report on Patentability in international application No. PCT/EP2007/063347 filed on Dec. 5, 2007.
Jun. 10, 2009 Written Opinion of the International Search Authority in international application No. PCT/EP2007/063347 filed on Dec. 5, 2007.
Apr. 6, 2009 Advisory Action for U.S. Appl. No. 10/483,020, filed Mar. 31, 2004.
Apr. 6, 2009 Non-Final Office Action for U.S. Appl. No. 10/490,752, filed on Jul. 21, 2004.
Feb. 1, 2010 Advisory Action for U.S. Appl No. 10/580,200, filed Mar. 30, 2007.
Jan. 28, 2009 Notification of Reasons for Rejection in JP 2003-509960.
Jul. 11, 2008 Notification of Reasons for Rejection for corresponding JP 2003-509960.
Mar. 16, 2010 Final Office Action for U.S. Appl. No. 10/483,020, filed Mar. 31, 2004.
Mar. 2, 2010 Non-final Office Action for U.S. Appl. No. 10/580,200, filed Mar. 30, 2007.
PCT/EP2007/063347 filed on Dec. 5, 2007 Preliminary Examination mailed Jun. 10, 2009.
Sep. 14, 2009 Office Action in Japanese patent application No. 2003-509960.
Sep. 30, 2008 Final Office Action in U.S. Appl No. 10/490,752 filed on Jul. 21, 2004.
U.S. Appl No. 12/730,621, filed Mar. 24, 2010 Final Office Action dated Jul. 6, 2012.
U.S. Appl. No. 12/730,621, filed Mar. 24, 2010 Non-Final Office Action dated Mar. 21, 2012.
U.S. Appl. No. 10/483,020, filed Mar. 31, 2004 Final Office Action dated Sep. 13, 2010.
U.S. Appl. No. 10/580,200, filed Mar. 30, 2007 Final Office Action dated Sep. 1, 2010.

* cited by examiner

TRANS-LUMINAL SURGICAL DEVICE

PRIORITY

This application is a U.S. national stage application under 35 USC §371 of International Application No. PCT/EP2004/00248, filed Jan. 15, 2004, claiming priority to United Kingdom Patent Application No. 0300915.6, filed Jan. 15, 2003, and to United Kingdom Patent Application No. 0327306.7, filed Nov. 24, 2003, each of which is incorporated by reference in its entirety into this application.

TECHNICAL FIELD

This invention relates to a trans-luminal surgical device and more particularly, but not exclusively, to a stent pusher assembly, and to a delivery system having a rapid-exchange configuration for deploying a self-expanding stent at a stenting site within a human or animal body.

BACKGROUND ART

EP-A-1 095 634 (EP 634) discloses a rapid-exchange, self-expanding stent delivery system. EP 634 discloses a system in which the soft atraumatic distal tip of the system is at the leading end of the inner catheter. The outer sheath of the delivery system has a distal end which stops proximally short of the atraumatic tip.

Stents to be deployed at a stenting site within a human or animal body expand radially in the course of delivery, from a radially compact delivery disposition to a radially larger deployed disposition. In self-expanding stents made of stainless steel, the deformation of the stent is below the elastic limit, the stent until its deployment being radially confined and under elastic stress and typically released by proximal withdrawal of a confining sheath while the stent is itself prevented from moving proximally with the confining sheath by abutment with a stop on the distal end of a catheter shaft which suffers axial compressive stress while the surrounding sheath is proximally withdrawn.

By contrast, stainless steel stents which are relaxed in a radially compact disposition suffer plastic deformation when expanded into their deployed disposition by inflation of a balloon within the lumen of the stent.

An early example of stainless steel self-expanding stents is Gianturco U.S. Pat. No. 4,580,568 and an early example of the balloon expansible stainless stent is Palmaz EP-A-221 570.

A third category of stent is the memory metal stent, made of a biologically compatible nickel-titanium shape memory alloy with martensitic and austenitic phases. At body temperature, the stent "seeks" to revert to the austenitic phase. Typically it is confined within a surrounding sheath and again released at the stenting site by proximal withdrawal of this sheath.

The present invention offers improvements in systems to deliver those stents which are brought to the stenting site within a confining surrounding sheath.

In the technical field of stenting, there is a desire to reduce the transverse dimensions of the stent delivery system. In this field, the widely used measure of transverse cross-section is the unit of "French", often abbreviated to "F" which is a one third part of a millimeter. Thus, a 6 French (6 F) delivery system has a diameter of 2 millimeters.

For any particular stenting operation, one has to select a particular stent and a particular delivery system. There is a large choice in both of these elements. Accordingly, it would be an advantage for manufacturers of stents and their delivery systems to achieve a degree of modularity in the design and construction of stents and their delivery systems. For example, there is a wide range of stents which could be delivered by a 6 F delivery system and it would therefore be convenient for the manufacturer of a stent delivery system to be able to tailor a basic 6 F system to fit any particular stent which would be compatible with a 6 F delivery system. This would reduce costs, to the advantage of patients, while retaining full flexibility for medical practitioners to optimise their choice of stent for any particular patient.

Like many catheter systems and trans-luminal surgical devices, a stent delivery system is often used with a flexible guidewire. The guidewire is preferably made of metal, and is slidably inserted along the desired body passage. The delivery system is then advanced over the thus pre-placed guidewire by "backloading" or inserting the proximal end of the guidewire into a distal guidewire port leading to a guidewire lumen defined by the delivery system.

Many conventional trans-luminal surgical devices delivery systems define guidewire lumens that extend along the entire length of the outer sheath. These delivery systems are described as "over-the-wire" delivery systems, in that the surgical device is guided to the site of the surgery over the guidewire, the guidewire thereby exiting the delivery system at the proximal end of the delivery system. "Over-the-wire" delivery systems provide several advantages, including improved trackability, the ability to flush the guidewire lumen while the delivery system is inside the patient's body, and easy removal and exchange of the guidewire while the delivery system remains in a desired position in the patient.

In some circumstances, however, it may be desirable to provide a "rapid exchange" delivery system, which offers the ability more easily to remove and exchange the delivery system while retaining the guidewire in a desired position within the patient. In a rapid-exchange delivery system, the guidewire occupies a lumen located only in the distal portion of the delivery system. The guidewire exits the delivery system through a proximal guidewire port, closer to the distal end of the delivery system than to its proximal end, and extends in parallel along the outside of the proximal portion of the delivery system.

Because a substantial length of the guidewire is outside the delivery system, it may be manually held in place close to the point where it passes the entry point on the body of the patient, as the delivery system is removed. This facilitates handling, removal and exchange of the delivery system for the practitioner for the following reasons.

With a guidewire lumen that is much shorter than the full catheter length a single physician can insert and remove a stent (or other surgical device) delivery system into and from the patient's body. Whereas conventional delivery systems require a guidewire having a length at least double the length of the outer catheter, the rapid-exchange configuration allows the use of much shorter guidewires which enable a single physician to handle the proximal end of the guidewire at the same time as the catheter at the point of its entry into the body of the patient.

Accordingly, the present invention advantageously provides a stent delivery system having a rapid-exchange configuration for delivering and deploying a self-expanding stent or other trans-luminal surgical element, or performing a surgical procedure in a percutaneous, trans-luminal manner.

Stents themselves cannot be directly seen by the naked eye during a trans-luminal journey to the stenting site, nor can one directly see whether the stent is exactly located as desired within the stenting site. Rather, indirect means have to be used to follow the progress of the stent through the body and make sure that it is correctly located before it is deployed. Thus, the device delivery system is used during deployment to carry radiopaque contrast or marker fluid to the site of surgery so that the target site can be seen through the radiopaque fluid in the bodily lumen at the site. This radiopaque fluid is generally injected through an injection port at the proximal end of the delivery system and through an annular space between an outer sheath of the delivery system and a proximal portion of an inner catheter shaft. The visibility of the site is adversely affected when the lumen, through which radiopaque contrast fluid is injected, is too small at the site to deliver a strong pulse of contrast fluid. As pulses of fluid are used for visualisation, the effectiveness of visualisation depends on the volume flow in each pulse. This in turn depends on the ease of flow of the fluid along the full length of the delivery system, from the point of injection at the proximal end, to the site of surgery beyond the distal end of the delivery system.

Thus, delivery systems which offer a large cross-section and unimpeded lumen for contrast fluid will be favoured by radiologists, other things being equal. The visibility can additionally be increased by further reducing the resistance of the system to pulses of contrast fluid. It is therefore an object of the present invention to provide good visualisation with contrast fluid, without sacrifice of other important performance aspects of the delivery system, including pushability and low overall diameter. By increasing "pushability" we mean the capability to be advanced longer distances along narrower and more tortuous bodily lumens.

Furthermore, the delivery system invariably carries at least one radiopaque marker at a known location relative to the length of the surgical device (such as a stent), so that radiologists can be sure of the location of the ends of the device, on the basis of their knowledge of the location of the radiopaque marker. Even if the device is rendered sufficiently radiopaque for it to be seen, it is still useful to have a radiopaque marker on the distal end of the delivery system, to reveal for example successful separation of the device from the delivery system.

Thus, in our example of a 6 F delivery system, to be used for delivering stents of various lengths, there will be a wish to provide radiopaque markers within the delivery system at two spaced-apart locations on the axis of the delivery system, corresponding to the opposite ends of the stent (until the stent is deployed out of the system). One object of the present invention is to offer a degree of modularity in this design aspect.

With delivery systems having a rapid-exchange configuration, just as with over-the-wire systems, the delivery system is advanced over the guidewire, itself normally within a guide catheter, in order to bring the distal tip and surgical device to the site of surgery. Depending on the application, different diameter guidewires are specified. Two commonly used guidewire diameters are 0.46 mm/0.018 inches and 0.89 mm/0.035 inches (commonly known as 18 thou or 35 thou guidewires). Thus, a further degree of modularity can be achieved by offering a delivery system which is compatible with a range of guidewire diameters, specifically, both 18 thou and 35 thou guidewires.

Naturally, it would be an advantage for any new stent delivery system to be able straightforwardly to take the place of those previous delivery systems which individual practitioners have grown to be comfortable using. One such system uses in its proximal shaft portion a metal "hypo" tube, which can be made of stainless steel or another biocompatible alloy such as the cobalt/chromium/nickel alloy known by the trademark PHYNOX. The tube usually contains a push rod and the tube and rod move axially relative to each other to release the stent.

Further, it goes almost without saying, that good design for delivery systems for surgical devices such as stents is indicated by manufacturing steps which can be performed with high precision and reliability, yet with acceptable cost levels. This is yet another objective of the present invention.

Finally, for any system which is extremely long in proportion to its diameter, and features at least three co-axial elements, the cylindrical surfaces of these co-axial elements need to be so composed and conformed that friction between them is low enough that the co-axial elements can be moved tolerably easily axially relative to each other. It is yet another object of the present invention to provide systems which offer possibilities for bringing these friction levels down to advantageously low levels.

Along with all these issues already appreciated by those skilled in the art, there is a further performance aspect which becomes evident when a self-expanding stent is released progressively by successive proximal stepwise movements of the outer confining sheath.

Typically, the delivery system is extremely long in proportion to its cross-sectional dimensions, and is constructed predominantly or wholly from synthetic polymeric materials which have substantial elasticity and marked kinetic aspects to their deformation characteristics. In such a case, any particular rate of strain imposed on the proximal end of the outer sheath is likely to be experienced at the distal end of the same sheath in a somewhat different strain rate. For example, a fast squeeze of the trigger of a deployment system at the proximal end of the sheath will likely result in a somewhat slower resulting proximal advancement of the distal end of the same sheath. Furthermore, a pull on the sheath will impose compressive stresses along the length of the inner shaft, likely leading to a proximal movement of the stent which then relaxes back to the original, more distal, position of the stent as the tensile stress in the outer sheath eases back towards zero. In its own delivery systems, Applicant has observed what happens at the distal end of a stent delivery system during successive squeezes of the trigger of a delivery system which pulls the outer sheath proximally in a series of steps. The appearance at the stent end of the system is as if the system were "breathing" in that it, and the stent, moves axially first proximally, then distally, with each squeeze of the trigger.

This "breathing" phenomenon is of course a complicating factor when it comes to precision of intra-luminal placement of a stent (or other surgical element) within any particular luminal site of surgery. It is yet another object of the present invention to ameliorate this problem.

Relevant disclosures of intra-luminal surgical element deployment system are disclosed in Applicant's earlier WO 01/34061 (WO 061) and WO 03/003944 (WO 944) the contents of which is hereby incorporated by this reference. For placement of a stent, the system may include an annular pusher element which abuts the stent to stop it moving proximally when the outer sheath is withdrawn proximally to release the stent.

In one embodiment of the system disclosed in WO 944 there is included a pusher assembly for a delivery system for a self-expanding stent, the pusher assembly constituting a catheter shaft with a proximal pusher end to receive an endwise compressive force and a distal pusher end to deliver said force to a stent to be delivered, the pusher assembly comprising a pusher strand extending from the proximal pusher end to a distal strand end which is nearer the distal pusher end than the proximal pusher end; a pusher element which abuts the stent in use to deliver said force to the stent; and a transfer shaft having a proximal and a distal end, the proximal end being connected to the distal tube end and the distal end being connected to the pusher element and wherein the pusher element defines a guidewire path, and the transfer shaft lies to one side of said path.

By contrast, in conventional systems such as that of EP 634 in which the atraumatic tip is carried on the inner catheter, the pusher element is mounted on a tube which has a guidewire lumen and extends distally all the way to the tip.

Embodiments of the system of WO 944 provide a stent delivery system having a rapid-exchange configuration for a self-expanding stent which provides improved visualisation through an increased volume flow in each pulse of radiopaque contrast medium pumped through the device. The volume flow in each pulse is increased in the present invention due to a simplified and reduced internal structure of the delivery system.

The fundamental disclosure of Gianturco U.S. Pat. No. 4,580,568 reveals the essential features of a basic delivery system to be an outer sheath confining a stent in a radially compressed state and a pusher element preventing proximal movement of the stent when the outer sheath is proximally withdrawn. The pusher element is carried on an inner catheter shaft. The delivery system is inserted over a guidewire into a lumen of a human or animal body.

A preferred embodiment of the system of WO 944 gets back some way towards the simplicity of such a delivery concept by shortening the inner catheter shaft so that its distal end is relatively close to the proximal guidewire lumen exit port. By contrast, in the by now conventional tip arrangement of a self-expanding stent delivery system the inner catheter shaft extends more distally, even beyond the distal end of the stent, to provide a tapered tip, for ease of insertion of the delivery system into the patient's body and for reducing trauma whenever the catheter is advanced distally. Abovementioned EPO 634 discloses a stent delivery system which conforms to this conventional model.

In preferred embodiments of the system of Applicant's WO 944, the stent pusher element carries a carrier tube which is used to define at least a short distal guidewire lumen. Further, a system tip taper on the distal end of the outer sheath, renders redundant the need for an atraumatic distal tip on the inner catheter distal of the stent. Therefore, the internal structure of the delivery system is more open, which consequently enhances ease of flow and the volume of contrast fluid that can be ejected from the distal end of the delivery system with each successive pulse imposed from the proximal end of the delivery system. Hence, visualisation is improved.

The manufacturing and assembling steps required to get the delivery system ready for use are minimized due to the simplified internal structure. No longer is there a necessity for keeping the stent at a fixed position on the inner catheter shaft while the outer sheath is fitted over the stent. Also, the risk of advancing the stent too far distally and out of the distal opening of the outer sheath during assembly of the delivery system is minimised, since the outer sheath preferred in embodiments of WO 944 comprises the tapered tip which acts as a distal stopper for the stent during assembly. Also, it is worthwhile to note that there are fewer steps during manufacturing and assembly of the stent delivery system, which itself is a valuable gain in this technical field.

The systems illustrated in Applicant's WO 061 and WO 944 include a self-expanding stent confined within a sleeve that has a heat-formed tapered distal tip. The stent is loaded into the sleeve from the proximal end of the sleeve and, upon deployment of the stent, the tapered tip is drawn proximally over the whole length of the stent to release the stent progressively.

The introduction of a stent using a preferred embodiment of the stent delivery system of WO 944, and subsequent removal of the delivery system, is facilitated especially in tortuous vessels and other body lumens having a relatively narrow diameter because, once the stent has been placed at a desired site inside the patient's body, there need be no component of the delivery system which is radially inwardly located from the stent and which has to be proximally withdrawn through the stent lumen. Especially in narrow and sharply curved body vessels, this might introduce a risk that the distal tip being withdrawn through the stent lumen interferes with bodily tissue protruding radially inwardly through the interstices of the stent and into the stent lumen. A preferred delivery system avoids this problem by providing the tapered tip on the distal end of the outer sheath so that, during removal of the delivery system out of the patient's body, there need be no system components which travel proximally within the stent lumen and are likely to engage with the inner surface of the stent.

In one preferred embodiment revealed in WO 944, the pusher element is a cylinder which has a distal-facing end face at the distal end of the cylinder to push on the proximal end of the stent. The end face is flat and transverse to the axis of the cylinder. The pusher element can serve as, and preferably does serve as, a radiopaque marker.

If desired, the pusher element can also serve as a mount for a distal marker carrier tube cantilevered distally forward from the pusher element to lie within the space that will correspond to the lumen of the stent to be deployed by the system. This is useful when it is required to have on the delivery system a radiopaque marker for the distal end of the stent. This radiopaque marker can be placed on the carrier tube at a position at or towards the distal end of the carrier tube and corresponding to the distal end of the stent. For stents of different lengths, the length of the carrier tube can easily be varied to correspond to the stent length, prior to fixing the distal marker on the carrier tube.

It will be appreciated that the carrier tube requires relatively little strength, so can be made thin and flexible, thereby reducing the risk of its interfering with tissue protruding through the stent during its withdrawal from the stenting site.

As the carrier tube is a relatively simple and isolated part of the delivery system, and conveniently made of a synthetic polymeric material, it will be a relatively simple matter to change the length of the carrier tube to suit any particular stent destined to be carried on the system. If desired, the carrier tube can be extended backwards proximally from the pusher element and given an end flared outwardly proximally. This flared end provides security against the possibility of unwanted slippage of the carrier tube distally through the pusher element and of being left behind in the body when the delivery system is withdrawn. It may also be useful to guide the guidewire through the system whenever there is need to introduce the distal end of the guidewire from the proximal end of the system.

Another option for modularisation is given by a transfer shaft connecting the rod or inner catheter with the pusher element. This can be set to any desired length, to accommodate stents of different length in a delivery system which features standard length catheter components such as the sheath, rod or inner catheter and pusher tube. It may be convenient to use a welded joint to fasten one or both of the two ends of the transfer shaft to the pusher element and rod, respectively.

SUMMARY OF THE PRESENT INVENTION

The present invention is an improvement in, or modification of, the system disclosed in Applicant's earlier WO 944. The system of the present invention can be used for purposes other than delivering a self-expanding stent. Further:

i. the distal end of the outer sheath need not be tapered, with any desired taper being provided on an inner shaft instead; and ii. the proposals of WO 944 for modular construction need not be included.

The present invention is defined, in one aspect, in claim 1 below. In another aspect, the present invention features the step of imposing a radially-inward taper on the proximal end of a sleeve which is itself at the distal end of a trans-luminal, guidewire-advanced, rapid-exchange surgical delivery device, the taper defining a proximal guidewire lumen exit port.

In one embodiment, a mandrel is used to define the exit port, as the taper is imposed. The mandrel is conveniently a pin, lying in the path which the guidewire should occupy, but with a diameter slightly larger than the contemplated guidewire.

The taper can be imposed by a combination of heat and radially-inward pressure. Heat-forming the sleeve in a proximal end zone thereof is one possibility to impose the said taper. Heat shrinking with the mandrel in place is particularly preferred. Heat-shrinking the sleeve over a distally-directed shoulder of the delivery system is an effective way to build a push-compatible connection between the distal end of a shaft of the delivery device and the proximal part of the sleeve of the device. Equipment suitable for accomplishing the desired heat-forming step is obtainable from Engineering and Research Associates, Inc. which does business as SEBRA. SEBRA is at 100 North Tucson Boulevard, Tucson, Ariz. 85716, USA and www.sebra.com.

If the sleeve is reinforced with filamentary material such as a metal braid, and if the sleeve defines an atraumatic tip of the surgical delivery device, then it will normally be appropriate to terminate the filamentary material proximal of the inwardly-tapering tip. At the inwardly tapered proximal end zone of the sleeve, it may be attractive for a metallic braid or other filamentary reinforcing material to remain, so as to enhance the connection in tension between the sleeve and the shaft. In the case of a mesh embedded in the wall thickness of a sleeve of synthetic polymeric, heat-softenable material, heat-forming of the proximal taper can allow the crossing angle of the braided filaments to change, as the tube defined by the braid in the tapered proximal zone reduces its diameter and increases its length. As mentioned above, such filamentary reinforcement, especially braiding, can help to obviate or ameliorate the "breathing" phenomenon users experience when trying to deploy, in a series of sleeve-withdrawing pulls, a self-expanding stent into a bodily lumen.

In preferred embodiments of the delivery device of the present invention, its primary shaft is a tube. That tube may contain an inner shaft which, in use, slides relative to the tube, whereby the imposition of endwise compression on the inner shaft, and endwise tension on the tube, withdraws the sleeve proximally relative to the distal end of the inner shaft. In other embodiments, the endwise compression is suffered by the tube and the endwise tension is imposed on a pull wire within the tube of the shaft. Indeed, such an arrangement has advantages, explained below. Typically, the distal end of the inner shaft is configured as a pusher, for maintaining the position of a surgical element at the site of surgery, during proximal withdrawal of the sleeve to expose the surgical element to the bodily lumen along which the delivery device has been advanced to the site of surgery. Otherwise, the tube of the primary shaft can be connected to such a pusher. The surgical element is typically a self-expanding stent, of a biologically compatible material such as a nickel-titanium shape memory alloy.

When assembling the delivery system, it may be convenient first to form the distal tip of the sheath, then to load the stent into the lumen of the sheath from its proximal end, then to advance the inner catheter components into the sheath proximal of the stent, and finally to form the inwardly tapered proximal end of the sheath.

Conveniently, the guider tube of the device extends distally beyond the distal end of the primary shaft of the delivery device. It may be useful to include a guidewire guider hose which has a proximal end and a distal end, and a lumen which is contiguous with the lumen for the guidewire in the guider tube, the proximal end of the guider hose being contiguous with the distal end of the guider tube. Conveniently, the distal end of the guider hose is flared radially outwardly, towards the luminal wall of the sleeve so that, when the proximal end of a guidewire is back-loaded into the distal end of the sleeve of the delivery device, the outward taper gathers the proximal end of the guidewire into the lumen of the guider hose (and thereafter through the guider tube and out through the proximal guidewire lumen exit port). Preferably, the distal end face of the guider hose occludes substantially all the sheath lumen and has one lumen for the guidewire and a separate lumen for the inner catheter shaft. With careful shaping of the end face into an inclined ramp surface, the proximal end of a guidewire being back-loaded into the guidewire lumen can be guided into the guider hose lumen by the ramped end face.

It is contemplated that the structure of the distal end of the inner shaft, through to the distal tip of the delivery device, may be freely adopted from the inner shaft constructions disclosed in Applicant's earlier WO 944, including such features as an annular surgical element pusher which defines a portion of the length of the guidewire lumen and which is aligned with the lumen for the guidewire at the distal end of any guider hose. The pusher might carry a carrier tube which extends distally from the annular pusher and itself defines a portion of the length of the guidewire lumen. The carrier tube might carry a radiopaque marker band at or near its distal end and the carrier tube might extend proximally from the annular pusher into a portion that tapers outwardly towards the luminal wall of the sleeve for guiding into the carrier tube the distal end of a guidewire advanced distally from the proximal guidewire exit port. There might be a connector between the inner shaft and the annular pusher, for facilitating modular assembly of delivery devices to suit different lengths of surgical element. Specifically, it will often be advantageous to find an unbroken metal strand running from the proximal end of the inner shaft to the annular shaft that is to engage on the surgical element due to be deployed from the delivery device.

For a better understanding of the present invention, and to show more clearly how the same may be carried into effect, reference is made to the accompanying drawing figures, as follows.

Component parts, to the extent that they correspond to component parts in the other drawing figures, may be identified by the same reference sign.

Figure 1:
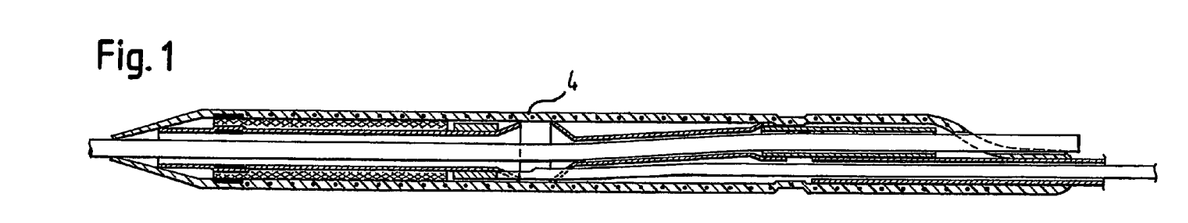
FIG. 1 shows a longitudinal diametral section through the distal end of a surgical delivery device in accordance with the present invention.

Looking at FIG. 1, what is shown is the distal part of a stent delivery system having a total length of the order of 1300 mm, the portion shown in FIG. 1 amounting to the distal-most 300 mm of the length of the entire system. As we see, this distal portion has an overall diameter of 5 F (French) whereas the shaft portion of the length of the system, proximal of the distal sleeve 4, has an overall diameter of about 1.8 F.

Figure 2A:
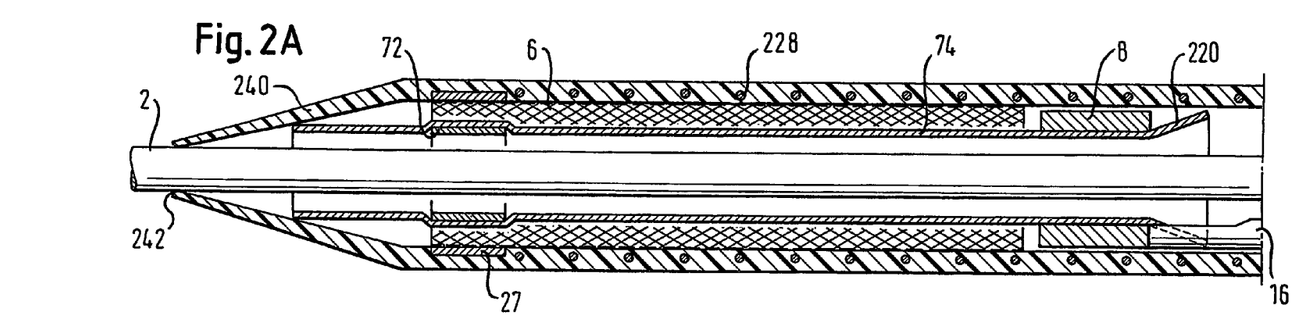
FIG. 2A is such a section, at greater magnification, of the distal portion.
Figure 2B:
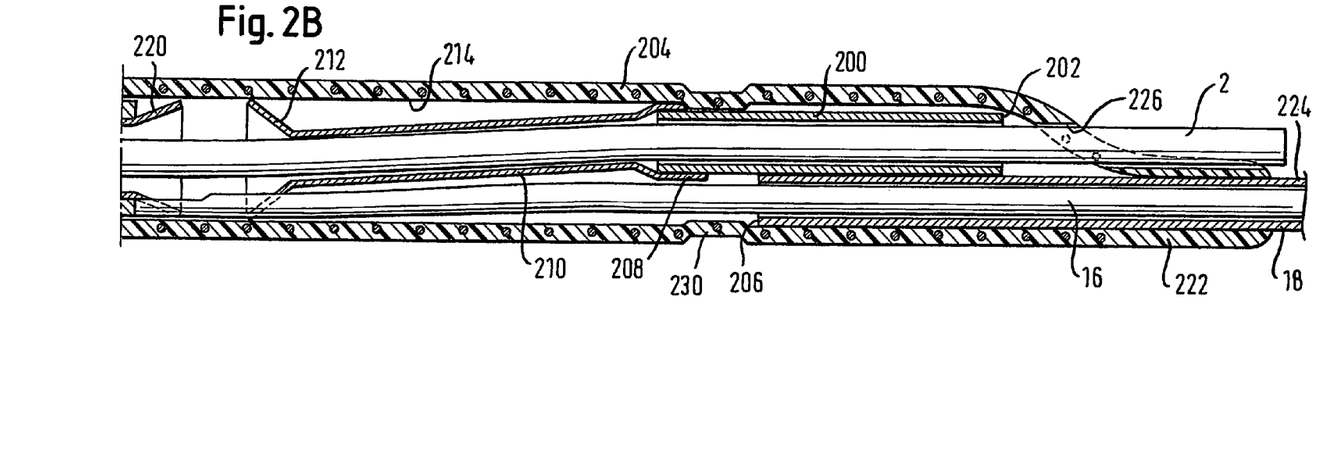
FIG. 2B the proximal portion, of the distal end shown in FIG. 1.

Now referring to FIG. 2A,B, for the details of construction of the system, its primary shaft 18 takes the form of a stainless steel hypo-tube. To the distal end of this tube is welded a stainless steel guidewire guider tube 200 which has a proximal end 202, a lumen, and a distal end 204 which is located distally of the distal end 206 of primary shaft 18. Form-fitted over the distal end of the guider tube 200 is the proximal end 208 of a synthetic polymeric guidewire guider hose 210 which defines a guidewire lumen and has a distal end 212 which is radially outwardly flared towards the luminal surface 214 of the sleeve 4 of the device.

Within the primary shaft 18 is an inner shaft 16 which extends distally forward, past the outward tapered end 212 of the guider hose 210, as far as an annular pusher element 8, to which it is welded. The inner shaft 16 is conveniently of stainless steel and conveniently welded to the annular pusher 8 which may also be of stainless steel. The pusher 8 can comprise, or even consist, radiopaque material such as tantalum, in order that the pusher ring 8 may serve as a radiopaque marker band. The annular pusher 8 carries a carrier tube 74, which itself carries a radiopaque marker band 72 and has a proximal end 220 tapered radially outwardly towards the luminal wall surface 214 of the sleeve 4, as described in above-mentioned WO 944.

Turning now to features that distinguish the present invention from the disclosure of WO 944, it is to be noted that the sleeve 4, at its proximal end 222, is tapered inwardly, to become form-fitted around the external cylindrical surface 224 of the primary shaft element 18.

FIGS. 1 and 2 show guidewire 2 in chain-dotted outline and it is to be noted that this location of the guidewire 2 extends through a proximal guidewire lumen exit port 226 found within the tapered proximal portion 222 of the sleeve 4. One convenient way to form the exit port 226 is with a mandrel (not shown) that takes the path of the guidewire, in the lumen of the guider tube 200, but which penetrates also the sleeve 4, and the embedded braiding 228, after the cylindrical wall of the sleeve 4 has been deformed over the proximal end 202 of the guider tube 200.

The mandrel is a simple pin, which extends into the lumen of the guider tube 200, and some way proximally of it, and has a diameter somewhat greater than that of the guidewire which in use of the system, will take the place of the pin.

With the mandrel having penetrated the sleeve wall and braiding, and extending into the guider tube 200 from its proximal end 202, the sleeve 4, at its proximal end, can be heat-shrunk down onto the primary shaft tube 18. After such heat shrinking, the mandrel can be removed, leaving the guidewire exit port 226 fully formed in the heat-shrunk proximal sleeve end, and aligned with the lumen in the guider tube 200.

Looking along the length of the sleeve 4, distally of the inwardly-tapered proximal zone 222, and at the zone 230 immediately distal of the distal end 206 of the primary shaft tube 18, we find another zone of radially inward heat shrinkage, around that part of the length of the guider tube 200 which protrudes distally beyond the distal end 206 of the primary shaft tube 18, yet proximal of the distal end 204 of the guider tube 200. This inwardly shrunk zone 230 is effective to resist any tendency of the sleeve 4 to slide proximally over the guidewire guider tube 200, for example when the delivery system is subject to compressive stress in the primary shaft tube 18, as when it is being pushed from its proximal end to urge the distal end, with the sleeve 4 along a bodily lumen.

The inward shrinkage can be manifested in a reduced outer diameter corresponding to greater frictional engagement between the sleeve and the shaft. Alternatively, or additionally, the sleeve inner diameter can be reduced, which would yield on its luminal surface a shoulder to resist proximal slippage of the sleeve in the shaft.

Additional security is obtained by swaging a ring of stainless steel or other swageable material, around the guider tube distal end and the shaft tube 16, to compress the material of the sleeve 4 just distal of the distal end of the shaft tube 16.

FIG. 2A, 2B shows a self-expanding stent 6 within the sleeve 4, and a tapered distal end 240 of the sleeve 4 as with the embodiments described in WO 944. Note that the embedded metallic filament braiding 228 in the sleeve 4 stops proximally short of a tapered atraumatic tip 240. Note that the atraumatic tip 240 of the sleeve 4 tapers down to a leading annulus 242 of the entire system, which has a diameter adapted to fit with relatively small clearance, or even snugly, around the cylindrical wall surface of the guidewire 2.

To assemble the stent 6 and the delivery device, the sleeve 4 is prepared with its proximal end not yet heat-formed. The stent 6 is introduced into the sleeve 4 at the open proximal end, and advanced along the length of the sleeve until it reaches its delivery disposition just proximal of the distal tip of the sleeve 4. Then the assembly of pusher 8 in a shaft 12/16 and primary shaft tube 18 is assembled together and all introduced as a sub-assembly into the open proximal end of the sleeve 4. Then a mandrel is advanced through the wall of the sleeve 4, as that wall lies over the proximal end of the guide tube end 202 of the guider tube 200, and advanced into the lumen of the guider tube 200. then, with the mandrel in place, the proximal end 222 of the sleeve 4 is heat-shrunk down onto the outside cylindrical wall 224 of the primary shaft tube 18, also with heat and radial inward pressure at the annulus 230 of the sleeve 4 just distal of the distal end 206 of the primary tube 18.

Those skilled in the art will be familiar with the usual arrangements at the proximal end of the coaxial tube 18/shaft 16 arrangement, for deploying the stent 6 by proximal retraction of the sleeve 4. Further details are available from WO 944. After proximal withdrawal of the sleeve 4, to deploy the self-expanding stent 6, the entire delivery system may be withdrawn from the bodily lumen and the body of the patient. It will be appreciated that the only component withdrawn proximally along the lumen of the expanded stent 6 is the carrier tube 74, which has minimal structural features to interfere with any bodily tissue protruding radially inwardly into the lumen of the expanded stent 6, through its expanded interstices. It will be appreciated that proximal withdrawal of the sleeve 4 causes the taper tip 240 to open up to a more cylindrical configuration, with a distal opening 242 big enough to pass over the abluminal surface of the stent 6 being deployed. It may be convenient to provide the taper tip 240 of the sleeve 4 with parting zones which are elongate in the axial direction of the system, enabling the taper tip 240 to split into two or more part-circumferential portions in relief of hoop stresses imposed within the taper tip 240 by its being pulled proximally over the stent 6. Any such parting will relieve the hoop stress and tensile stress within the sleeve 4 in general, thereby reducing the amount of tensile force necessary to be applied to the primary tube 18 at its proximal end, and in turn reducing the level of compressional stress carried by the inner shaft 16 and its continuation 12, as well as by the stent pusher 8.

It will be evident to skilled readers that the details of construction of the inner shaft 16 distal of the primary tube 18 can be selected to fit with whatever surgical element is to be delivered by proximal retraction of the sleeve 4. For example, in place of the stent might be means to direct a laser beam to a zone of bodily tissue within a site of surgery or one or more electrodes for electrical treatment of such tissue. Otherwise, there could be on the distal end of the inner shaft 16 a filter for bodily liquid flowing within the lumen along which the delivery system is advanced. For example, one might wish to use the illustrated system to deploy a filter for blood in the carotid artery. Such filters are known, and conveniently are made of nickel-titanium shape memory alloy. Otherwise, one envisages the provision of inner shaft 16 in the form of an inflation lumen, and the provision of a treatment balloon, such as an angioplasty balloon, on the distal end of the shaft tube 16. Other uses of the delivery system illustrated in FIGS. 1 and 2A,B will be evident to those skilled in the art.

The system illustrated in FIGS. 1 and 2A,B show three radiopaque markers 8, 72 and 27, whereby progressive proximal withdrawal of the sleeve 4 reveals progressive proximal movement of radiopaque band 27 from a position overlying band 72 to a position level with, or proximal of band 8. Again, it will be evident to skilled readers that other arrangements of radiopaque marker bands are possible and would be selected to suit the individual circumstances in which the delivery system is to be employed.

Figure 3:
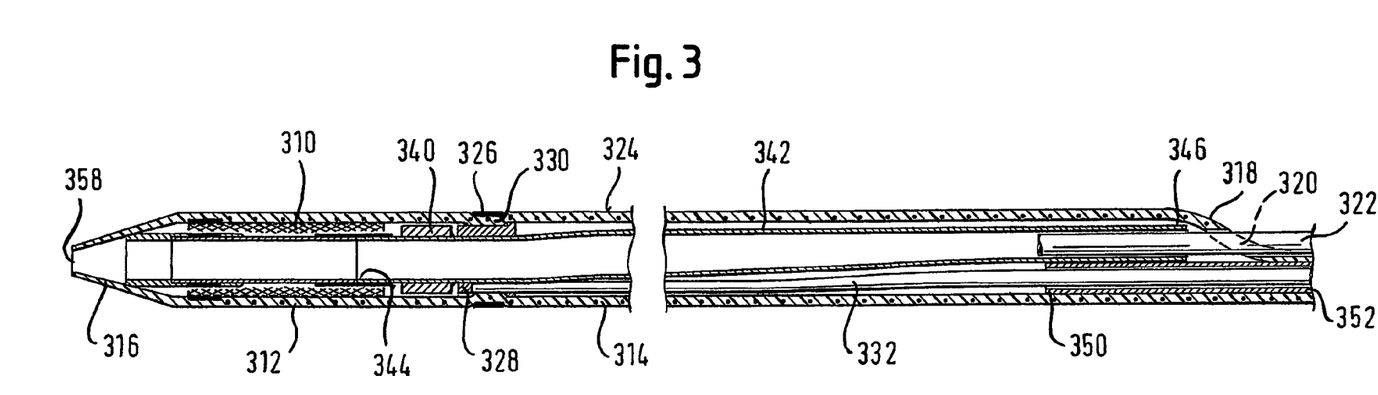
FIG. 3 is a longitudinal diametrical section through the distal end zone of a catheter device in accordance with the invention.
Figure 4:
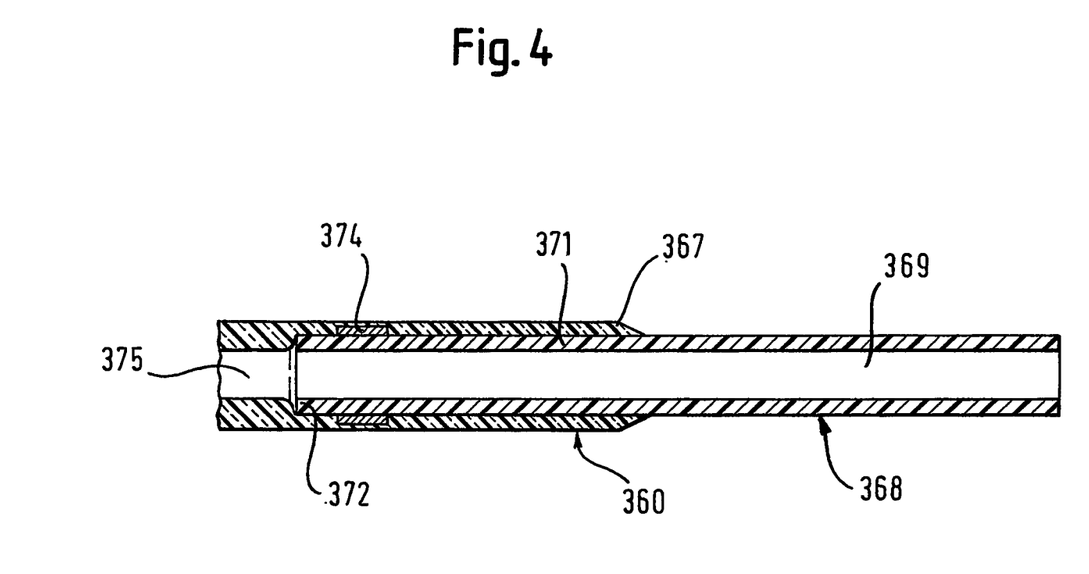
FIG. 4 is a longitudinal diametrical section, at enlarged scale, of the junction between the pusher tube and pusher tube extension of the embodiment of FIG. 3.

We turn now to the embodiment of FIGS. 3 and 4.

Figure 3A:
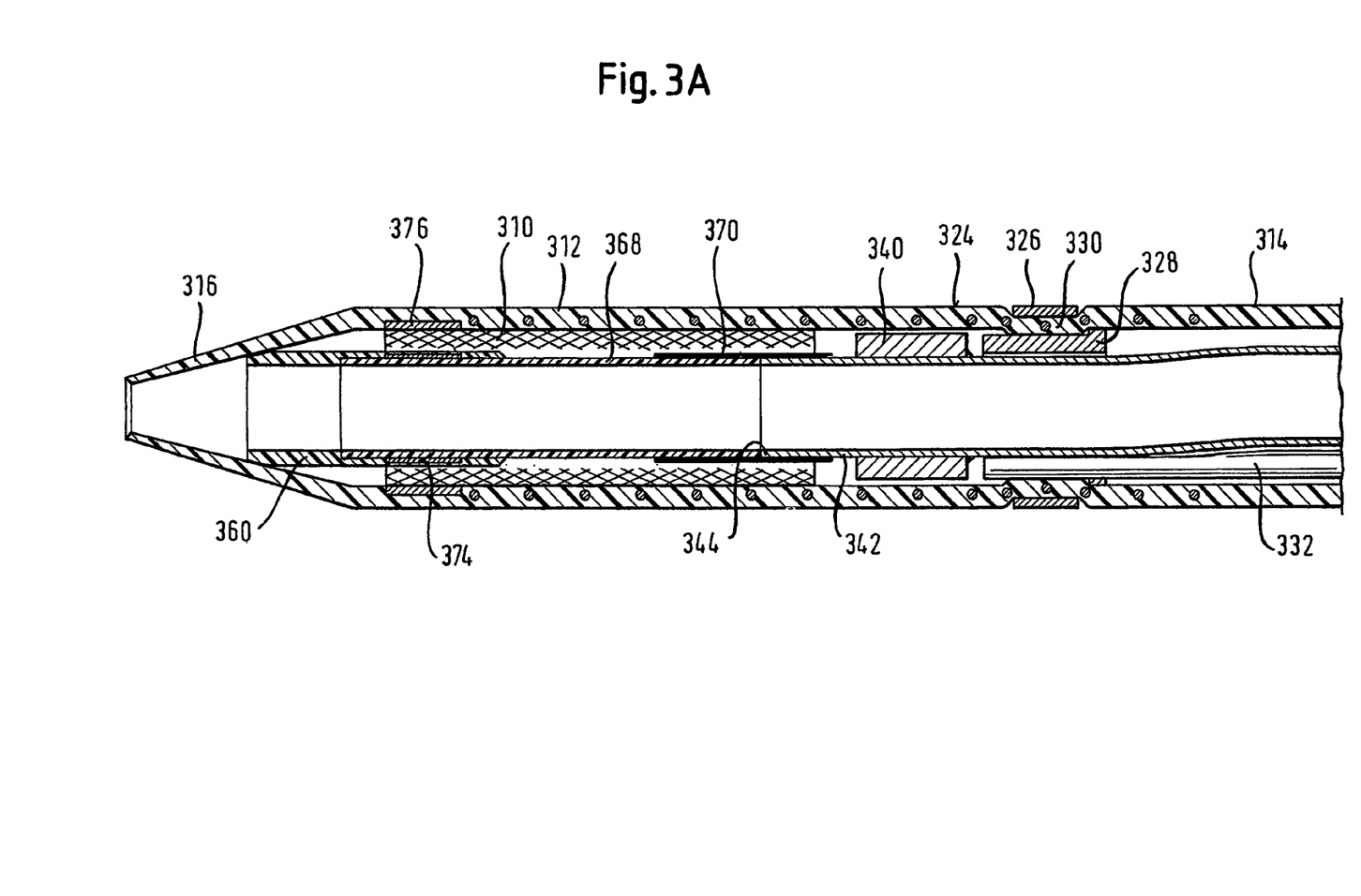
FIG. 3A is the identical section, at larger scale, through the distal part of the distal zone of FIG. 3.
Figure 3B:
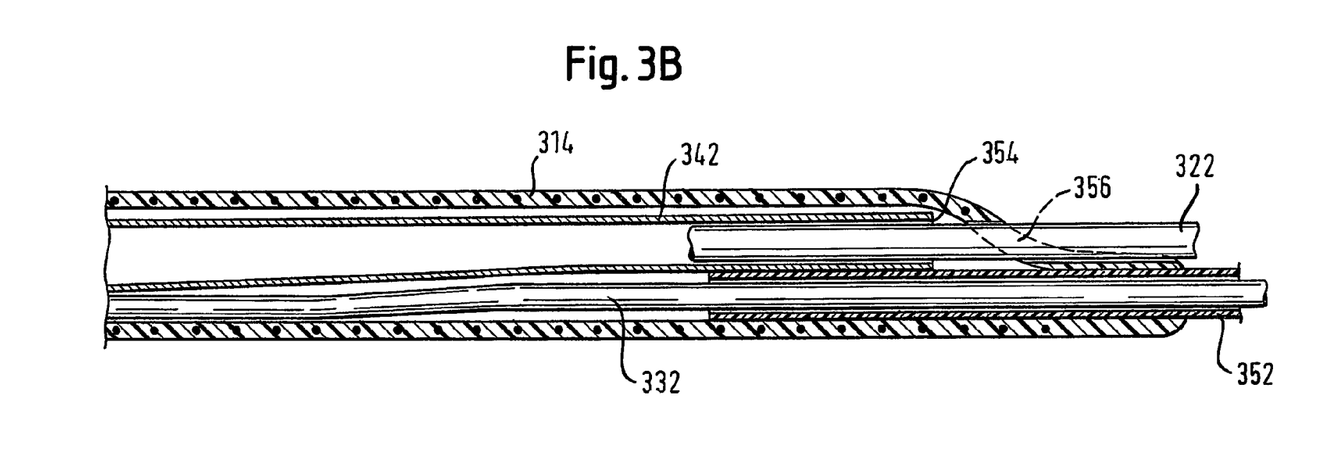
FIG. 3B is an identical section, at larger scale, through the proximal part of the distal zone of FIG. 3.

Referring to FIGS. 3, 3A and 3B, a self-expanding stent 310, or stent graft, lies inside the distal end zone 312 of a sleeve or sheath 314 with a tapered distal tip 316 and a heat-formed proximal end 318 which defines the orifice 320 of a proximal guidewire exit port for a guidewire 322. Being a self-expander, the stent 310 is, at least at body temperature, putting compressive stress on the luminal surface of the sleeve 314 in the distal end zone 312. Proximal of the stent 310, and on the abluminal surface 324 of the sleeve 314, is a swaged marker band 326 of radiopaque metallic material, which is pressing radially inwardly the material of the sheath 314 within the band 326. Radially inside the sheath at this point is a metal annulus 328 which is itself put under radially inwardly compressive stress by the material 330 of the sheath 314 inside the marker band 26. Thus, the sheath material 330 is compressed between metal bands inside (328) and outside (326) the sheath 314. Brazed to the annulus 328 is a pull wire 332 which runs from the annulus 328 all the way back to the proximal end of the catheter device, whereby endwise tensile stress imposed on the proximal end of the pull wire 332 will pull proximally the annulus 328 and thereby impose on portions of the sheath 314 distal of the annulus 328 an endwise tensile stress, for pulling the sheath 134 proximally with respect to the stent, to release the stent. At the same time, portions of the sheath 314 proximal of the annulus 328 will be pushed proximally.

A pusher annulus 340 is located in the lumen of the sheath 314 just proximal of the stent 310. Its purpose is to resist proximal movement of the stent 310, when the sheath 314 is withdrawn proximally from the stent 310. It can also serve as a radiopaque marker band to indicate the proximal end of the stent 310. The pusher annulus 340 is brazed or welded or otherwise fixed to a pusher tube 342 which is conveniently of a biocompatible cobalt alloy (PHYNOX™) and which has its distal end 344 distal of the pusher annulus 340 and within the lumen of the stent 310. The proximal end 346 of the pusher tube 342 is arranged side-by-side with the distal end 350 of a shaft tube 352 of the catheter device which extends all the way to the proximal end of the catheter device and is conveniently provided as a PHYNOX or stainless steel hypo tube. The lumen of this shaft tube 352 carries the pull wire 332. The overlapping portions 346 and 350 of the pusher tube and shaft tube are bonded to each other, conveniently by brazing, so that they effectively form a single metal strand from the proximal end of the catheter device to the stent pusher annulus 340. As can be seen in FIG. 3 and FIG. 3B, the end orifice 354 of the pusher tube 342 is co-linear with the orifice 356 in the heat-formed end 318 of the sheath 314, which defines the proximal guidewire exit lumen. Thus, when a guidewire 322 is advanced through the guidewire lumen of the catheter device by introducing it into the end orifice 358 of the tapered distal tip 316 of the sheath 314, the end of the guidewire will advance proximally along the pusher tube and exit through the port 356.

With reference to FIG. 3A and FIG. 4, we will now explain the structure of the pusher tube extension, distal of the pusher annulus 340, and located between that annulus and the end orifice 358 at the distal end of the sheath 314.

The metal pusher tube 342 extends for a short distance distally of the pusher annulus 340. A distal extension inner catheter 368 of polyimide abuts the distal end of the pusher tube 342 and is secured to that pusher tube by a shrink tube 370 radially overlying the distal end of the pusher tube 342 and the proximal end of the inner catheter 368. This shrink tube 370 is of PET (which shrinks radially downward to grip both these abutting portions).

FIG. 4 shows the distal end 372 of the distal extension inner catheter tube 368 and a bore 369 within it, open to the distal end of the inner catheter 368, and terminating proximally at an end-to-end butt joint with the distal end of the metal pusher tube 342. A tip extension catheter 360 of PEBAX polymer receives the distal end 371 of the inner catheter 368, so that its proximal end 367 overlaps the abluminal wall of the catheter 68. Around the distal end zone 372 of the catheter 368, and sandwiched between the distal catheter 368 and the proximal end zone of the tip catheter 360, is a second radiopaque metal marker band 374, and the whole assembly is bonded together with a cyanoacrylate adhesive composition. The PEBAX tip extension catheter 360 extends into the tapered lumen of the taper 16 of the distal end of the sheath 314.

Of note is that the bore 375 of the catheter 360 is contiguous and smooth with the bore 369 of the catheter 368 for smooth progress of a guidewire. Catheter 360 is soft and floppy but has a larger outside diameter than catheter 368, which helps to ease the end orifice of the sheath 314 open when it begins to withdraw. Proximal end 367 of catheter 360 is tapered inwardly. This is because, should a physician decide to sheath the distal end of the delivery system after stent deployment by re-advancing the sheath distally, the tapered tip 316 of the sheath is required to advance distally back onto the abluminal surface of catheter 360 and the taper 367 helps that advance.

Reverting to FIG. 3A, fixed to the lumen surface of the sheath 314, just proximal of the tapered tip zone 316, is a third radiopaque metal marker band 376 and it will be seen that this marker band lies radially outside the second marker band 374 within the distal extension inner catheter 368.

In use, the distal end zone of the catheter system, as shown in the drawings, is advanced along a bodily lumen to a stenting site. When all is ready for deployment of the stent 310, an endwise tension is applied to the pull wire 332, while the proximal end of the shaft tube 352 is restrained from endwise movement, reactive or otherwise. Endwise translation of the pull wire 332 results in proximal movement of the sheath 314. Holding the endwise position of the shaft tube 352 holds the endwise position of the pusher annulus 340 which in turn prevents any proximal movement of the stent 310 with the proximally withdrawing sheath 314.

Progressively, the sheath 314 withdraws proximally relative to the stent 310, having the effect of stretching the distal tip 316 of the sheath 14 over the radially outward surface of the stent 310, leading to progressive release and radial expansion of the stent 310, from its distal end toward its proximal end.

Note that, before there is any relative movement of the sheath 14 and pusher annulus 340, the radiologist "sees" only two marker bands, namely the first marker 340 and the radially superimposed second and third marker bands 3374 and 376. However, once the sheath 314 starts to withdraw proximally, the radiologist can see the third marker, at a position proximal of the second marker. Clearly, when the third marker has moved proximally to approach, pass over, and then move proximally away from the first marker 340, one has confirmation that the stent 310 has been deployed, by full proximal withdrawal of the sheath 314.

During proximal withdrawal of the sheath 314, it will be appreciated that the proximal end 318 of the sheath 14 slides proximally over the outside surface of the shaft tube 352.

It will appreciated that there should be no endwise movement of the shaft 352 relative to its surrounding entities, whether a bodily lumen or the lumen of a guide catheter, during deployment of the stent 310. This is an opportunity for enhancement of precision of the placement of the stent, because any friction between the outside surfaces of the shaft tube 352 and the surrounding structures will only tend to confirm the location of the pusher annulus with respect to the body of the patient, and thereby the location of the stent 10 with respect to the body of the patient.

Further, the friction forces between the pull wire 332 and the luminal surfaces of the shaft tube 352 ought to be very small or minimal, as should any frictional forces between the withdrawing sheath 314 and the outside surface of the shaft tube 352, at the proximal end 318 of the sheath. Further, as the sheath 314 is relatively short in proportion to the catheter device as a whole, any friction between the outside surfaces of the sheath 314 and the surrounding bodily tissue ought also to be usefully smaller than in conventional systems where the full length of the stent deployment catheter must be moved relative to its surroundings. All of this elimination of unwanted and unhelpful friction is advantageous to the person deploying the stent, because any tactile feedback should relate more closely to events at the stent itself, and any force input at the proximal end of the device should be more completely delivered to the components around the stent 310 at the distal end of the device. There should be less lost motion in the system between the proximal and distal ends, less hysteresis, and less discrepancy between the amount of force applied at the proximal end and the amount of force delivered to the components surrounding the stent. It should be possible, with the system proposed herein, to enhance the position of stent placement, and the degree of confidence that users have when deploying stents, that the stent has been deployed smoothly and correctly.

As to design variations, the following will be evident to those skilled in the art, but so too will many more design possibilities, within the relevant published state of the art but not mentioned here.

The sheath need not include braiding. The pull wire can be threaded directly to the braiding, thereby avoiding the need for any pulling annulus between the pull wire and the sheath. Neither the distal end nor the proximal end o the sheath need be tapered. An atraumatic tip to the device can be carried on the pusher sub-system that includes the stent stopper.

Implants to be delivered by the device need not be stents and stent graft. For example, filters can be deployed with the device.

Those skilled in the art will appreciate how to build an actuator for the proximal end of the device. A suitable basis is the device described in WO 02/087470, modified to accommodate the radial inversion of the push/pull elements.

It will be appreciated that, with the illustrated arrangement, there is no requirement for any axial movement of the outer shaft tube 352 relative to the bodily lumen in which it slides. Instead, since the shaft tube is connected to the stent stopper, it is required that there be no such axial movement. Accordingly, any binding between the shaft tube and any surrounding guide catheter, or bodily tissue of the access lumen, and any friction acting on the outside surface of the shaft tube, is turned by the present invention into an advantage rather than a problem, because it will help to confirm the axial position of the shaft tube relative to the stopper and the stenting site. The more tortuous the access lumen in the body, the more likely it is that there will be no axial movement of the shaft tube and stopper relative to the intended stenting site.

Furthermore, a shaft tube has more inherent resistance to elastic axial compression than a mere wire within the lumen of the tube. Thus, regardless how great are the tensile stresses imposed on the pull wire during the push-pull activity of stent release, there should be less unwanted proximal movement of the stopper from the intended site of stenting.

Furthermore, the means for pulling back the sheath can also be of metal and also with a high capacity to resist axial strain, increasing the precision with which the operator of the catheter device can control the progressive withdrawal of the sheath and release of the stent. Many doctors prefer to release a self-expanding stent in a step-wise movement. If the pulling system stretches, then a step-wise movement can have the consequence of a time-dependent response at the distal end of the system, and a relaxation of the pulling system between successive pulling steps, with consequent undesirable reverse distal movement of the sheath or else "lost movement" in the pulling system as it once again strains to take up the pull tension with successive step-wise pulls at the proximal end of the system.

Thus, the shaft tube 352 is conveniently a PHYNOX or stainless steel hypo tube and the pull wire 332 is conveniently of metal, such as a stainless steel wire, either solid or hollow. Furthermore, while the sheath will very likely be of polymer, it can be made resistant to elastic stretching during proximal withdrawal and release of the stent by embedding within the annular wall thickness of the polymer sheath a fiber reinforcement such as a braided metal mesh. In such an embodiment, there is effectively a continuous strand of elastic strain-resistant metal in the pulling system, all the way from the proximal end of the pull wire to the distal end of the polymer sheath, again adding to the precision of proximal withdrawal, and minimising any elastic strain within the system during withdrawal.

At the proximal end of the sheath, it will also be attractive to taper the diameter down to a relatively snug fit around the outside of the shaft tube (but not so snug as to resist proximal axial sliding of the sheath along the outside of the shaft tube). The proximal guidewire exit port is formed in the tapered proximal end of such a formed sheath, as explained above.

Distal of the stopper, the pusher tube is not required by the invention to carry any axial compressive stress and in any event should be soft and easily bendable so as to keep the catheter tip as floppy as possible. The compression resistant pusher tube could be extended distally beyond the stopper, all the way to the distal end of the sheath, in order to define a guidewire lumen which extends within the pusher tube all the way to the distal end of the system.

Indeed, the pusher tube could extend into an atraumatic tip distal of the distal end of the sheath. In this way, the tapered tip of the sheath could be omitted.

Figure 5:
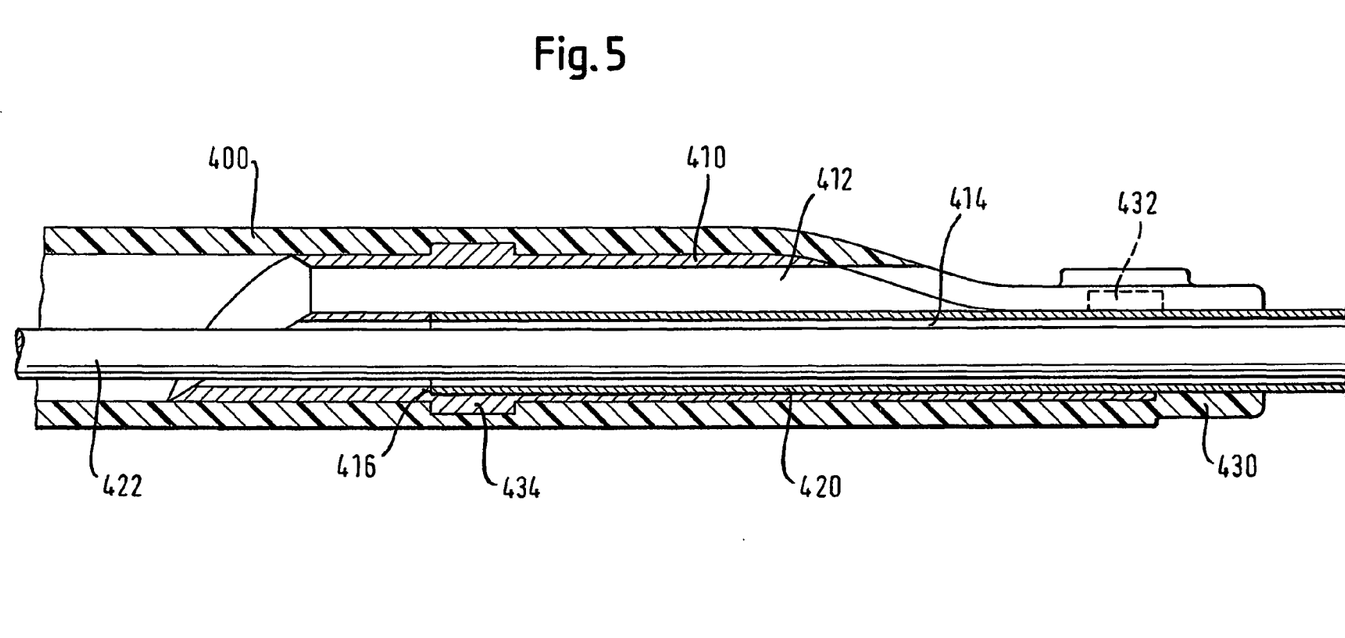
FIG. 5 is a longitudinal diametral section of a first variant.

FIG. 5 shows a variant. A sleeve 400 fits around a shaped member 410 which defines a guidewire lumen 412 and a primary shaft lumen 414. The distal end of a primary shaft tube 420 is received in the shaft lumen and abuts a shoulder 416 within that lumen. Within the shaft tube 420 is a push rod 422 that extends distally to a pusher annulus (not shown) for a self-expanding surgical device within the sleeve 400.

Thus, the sleeve is in tension when it is withdrawn proximally to release the device. It needs to be fixed reliably to the shaped member 410, as does the shaft tube 420 within its lumen 414. The proximal end 430 of the sleeve 400 is radially inwardly tapered down onto the outside surface of the shaft tube 420. The shaft tube 420 carries a protrusion 432 which is located on that side of the tube 420 where the guidewire lumen 412 is located, so as not to increase the passing diameter of the catheter, but is located also so as not to interfere with passage of the guidewire proximal of the guidewire lumen 412. Form-fitting the sleeve 400 over the protrusion 432 helps to anchor the sleeve against axial movement, in either direction, relative to the shaped member 410 or the shaft tube 420.

In addition, the shaped member includes protruding ring or set of protrusions 434 near the distal end of the shaped member and, again, the form-fitting of the sleeve over these protrusions will help to maintain the axial position of the sleeve relative to the shaped member without resorting to any adhesive composition. The shaft tube can be secured within the shaft lumen by any means the skilled person finds suitable. For example, if the shaped member and the shaft tube are both of metal then metal-to-metal joining techniques will be employed but if the shaft tube is of metal (such as stainless steel) and the shaped member of polymer then it may be advantageous to provide the distal end zone of the shaft tube with surfaces transverse to the shaft axis (recesses, holes in the tube wall, or protrusions) to be occupied by portions of the polymeric shaped member thereby to achieve a mechanical interlock. Other techniques will be known to those skilled in the art.

In other respects, details of the embodiments of the other drawing figures can be incorporated in the FIG. 5 variant.

Figure 6:
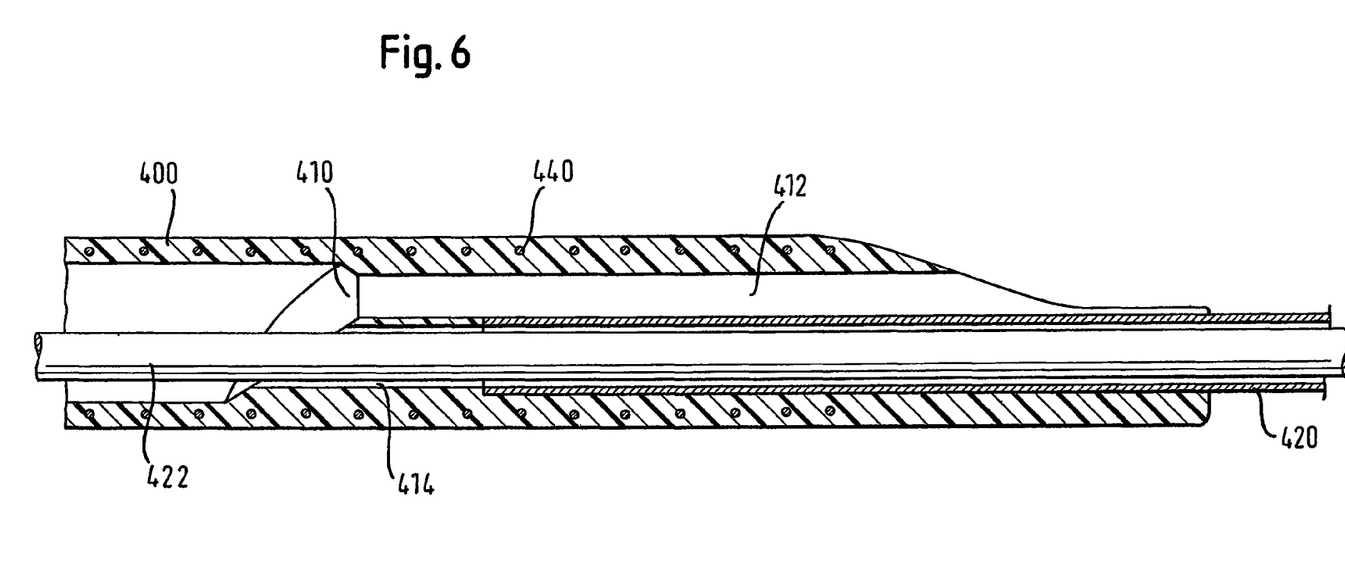
FIG. 6 is a longitudinal diametral section of a second variant.

FIG. 6 shows another variant. Components corresponding to the FIG. 5 embodiment carry the same reference numerals. Braiding 440 within the sleeve 400 stops short of the proximal end 442 of the sleeve. Both the sleeve 400 and the dual lumen shaped component 410 are made of PEBAX polymer and they are fused together by heat and pressure so that the cylindrical interface between them is no longer discernible. This fusion of course substitutes for the mechanical locking of the projections 432, 434 of FIG. 5. The shaft 420 can be fixed within its lumen 414 by any method known to the skilled person to be reliable enough to withstand the tensile stresses on the joint which it suffers during stent deployment.

The braided sleeve can be assembled by providing a suitable combination of cylindrical components on a mandrel and then imposing appropriate heat and pressure. For example, a three layer sandwich has been found effective. On the mandrel is first arranged a low friction PTFE cylinder, then a tubular braided mesh, then a PEBAX cylinder. On heating to render the PEBAX fluid, it flows around the braid filaments. On cooling the braid filaments are embedded in the PEBAX layer Although the presently preferred structures feature a sleeve with a tapered distal tip, and loading of the surgical device into the sleeve from its proximal end, this is not to exclude from this invention embodiments in which the sleeve has a cylindrical distal end past which the device is advanced proximally when it is loaded into the system.

The present Applicant has given the name "Dolphin" to the embodiments is has developed, because they exhibit at the proximal end of the sleeve a profile which is reminiscent of a dolphin nose, being caused by the side-by-side arrangement of abbreviated guidewire lumen and longer inner catheter lumen in the shaped element over which the sleeve is heat-formed.

Skilled readers will appreciate that technical features drawn from one or other of the illustrated embodiments can be carried into others of the illustrated embodiments. The illustrated embodiments are exemplary. The claims which follow define the scope of protection and bring out the spirit of the invention.

The invention claimed is:

1. A trans-luminal, guidewire-advanced, rapid-exchange surgical delivery device having a proximal end, a primary shaft and a distal zone to be advanced over a guidewire along a bodily lumen to a site of surgery, the device comprising:
   i. a guidewire tube defining a guidewire lumen, said guidewire tube lying within the distal zone with the guidewire lumen to one side of the primary shaft, the guidewire lumen having a length that longitudinally overlaps a length of the primary shaft and having a proximal end opening which lies to one side of the primary shaft; and
   ii. a sleeve comprising a unitary outer wall extending over an entire length of the sleeve, the sleeve defining only a single lumen, the sleeve lumen configured to receive a surgical element distal of the guidewire tube, a proximal end of the sleeve including a radially inwardly tapering portion over a proximal end opening of the guidewire tube, said inwardly tapering portion defining a proximal guidewire lumen exit port, and a tubular constant diameter nose portion surrounding the primary shaft proximal of the radially inwardly tapering portion, the nose portion defining a proximal-most end of the sleeve.

2. The delivery device according to claim 1, wherein said primary shaft is a tube.

3. The delivery device according to claim 2, wherein said tube contains an inner shaft which, in use, may slide relative to the tube, whereby the imposition of endwise compression on the inner shaft and endwise tension on the tube may withdraw the sleeve proximally relative to a distal end of the inner shaft.

4. The delivery device according to claim 3, wherein the distal end of the inner shaft is configured as a pusher, to maintain the position of said surgical element at said site of surgery during proximal withdrawal of the sleeve to expose the surgical element to the bodily lumen.

5. The delivery device according to claim 4, including the surgical element.

6. The delivery device according to claim 5, wherein the surgical element is a self-expanding stent.

7. The delivery device according to claim 3, wherein the guidewire tube includes a guider tube and wherein the guider tube extends distally beyond the distal end of the primary shaft.

8. The delivery device according to claim 7, and including a guidewire guider hose having a proximal end and a distal end, said proximal end overlapping the distal end of the guider tube, the guider hose and the guider tube being distinct components.

9. The delivery device according to claim 8, wherein the distal end of the guider hose is flared radially outwardly, towards the luminal wall of the sleeve.

10. The delivery device according to claim 9, wherein the inner shaft extends distally beyond the distal end of the guider hose, along a path between the abluminal wall of the guider hose and the luminal wall of the sleeve.

11. The delivery device according to claim 10, wherein the distal end of the inner shaft carries an annular surgical element pusher which is aligned with the lumen for the guidewire beyond the distal end of the guider hose.

12. The delivery device according to claim 11, wherein the annular pusher carries a carrier tube which extends distally from the annular pusher and itself defines a portion of the length of the guidewire lumen.

13. The delivery device according to claim 12, wherein the carrier tube carries a radiopaque marker band at or near its distal end at a position corresponding to the distal end of the surgical element.

14. The delivery device according to claim 12, wherein the carrier tube extends proximally from the annular pusher sufficiently far to define a portion which tapers outwardly towards the luminal wall of the sleeve, for guiding into the carrier tube the distal end of a guidewire advanced through the guidewire lumen distally, from the proximal guidewire lumen exit port.

15. The delivery device according to claim 10, wherein the inner shaft includes a connector, located axially between the distal end of the primary shaft and the annular pusher, said connector permitting adjustment of the axial position of the annular pusher relative to the distal end of the sleeve, during assembly of the device, to cater for different lengths of the surgical element.

16. The delivery device according to claim 15, wherein the inner shaft comprises a distal portion of solid cross-section and a proximal tube portion, the proximal tube portion extending within the primary shaft and distally therefrom, to said connector, or to a point proximal of said connector.

17. The delivery device according to claim 16, wherein the inner shaft exhibits an unbroken metal strand as far as the annular pusher.

18. The delivery device according to claim 3, wherein an annular surgical element pusher is disposed at the distal end of the inner shaft, the annular pusher being radiopaque and corresponding to a proximal end of the surgical element.

19. The delivery device according to claim 18, wherein the annular pusher carries a carrier tube which extends distally from the annular pusher and defines a portion of the length of the guidewire lumen, the carrier tube carrying a first radiopaque marker band at or near its distal end at a position corresponding to a distal end of the surgical element.

20. The delivery device according to claim 19, wherein a second radiopaque marker band is attached to the sleeve such that it slides proximally with the sleeve as the sleeve is withdrawn proximally to release the surgical element, the second radiopaque marker band capable of giving a radiographic indication of the progressive movement of the sleeve relative to the first radiopaque marker band and the radiopaque annular pusher.

21. The delivery device according to claim 20, wherein the second radiopaque marker band radially overlies the first radiopaque marker in an advancement configuration used for advancing the device along the bodily lumen.

22. The delivery device according to claim 1, wherein the sleeve is reinforced by filamentary material within a thickness of the outer wall.

23. The delivery device according to claim 22, wherein the filamentary material is braided material.

24. The delivery device according to claim 22, wherein the filamentary material stops distally short of the distal end of the sleeve.

25. The delivery device according to claim 1, wherein the distal end of the sleeve is tapered inwardly to provide the device, at least prior to its arrival at the site of surgery, with a more or less atraumatic tip.

26. The delivery device according to claim 25, wherein the sleeve is reinforced by a filamentary material within a thickness of the outer wall, and wherein the filamentary material stops distally short of the tapered distal end of the sleeve.

27. The delivery device according to claim 1, wherein the proximal end of the sleeve is form-fitted over the primary shaft by the application of heat and radially inward pressure, the proximal end of the sleeve, in profile, resembling a dolphin's head.

28. The delivery device according to claim 1, wherein the sleeve includes a push zone through which an endwise compression force imposed on a proximal end of the primary shaft can be transferred to the sleeve for advancing the sleeve along the bodily lumen to the site of surgery.

29. The delivery device according to claim 28, wherein the push zone is found immediately distal of the distal end of the primary shaft.

30. The delivery device according to claim 29, wherein the push zone corresponds to an annulus in which the sleeve has a reduced outside diameter relative to its diameter immediately proximal of said push zone.

31. The delivery device according to claim 29, wherein the push zone corresponds to an annulus in which the sleeve has a reduced inside diameter relative to its inside diameter immediately proximal of said push zone.

32. The delivery device according to claim 1, wherein a proximal portion of the guidewire tube is welded to a distal portion of the primary shaft.

33. A rapid-exchange delivery system, comprising:
a primary shaft having a proximal end and a distal end;
a guidewire tube attached to the primary shaft such that a length of the guidewire tube longitudinally overlaps a length of the primary shaft; and
a sleeve having a unitary outer wall extending over an entire length of the sleeve defining one and only one lumen, the sleeve including a distal section surrounding a self-expanding stent and a proximal section surrounding the guidewire tube, the proximal section including:
an annulus distal of the primary shaft distal end and adjacent thereto, the annulus having a diameter less than a diameter of the sleeve immediately proximal and distal of the annulus; and a tapering portion adjacent a proximal end opening of the guidewire tube and including a guidewire exit port aligned therewith, the tapering portion and annulus together preventing premature sliding of the sleeve with respect to the primary shaft and guidewire tube.

34. The rapid-exchange delivery system according to claim 33, wherein the sleeve comprises an outer PEBAX layer and an inner PTFE layer extending over an entire length thereof.

35. The rapid-exchange delivery system according to claim 34, wherein a braided mesh is embedded in a length of the outer PEBAX layer less than an entire length thereof.

36. The rapid-exchange delivery system according to claim 33, wherein the proximal section of the sleeve includes a tubular nose portion surrounding the primary shaft proximal of the tapering portion.

37. The rapid-exchange delivery system according to claim 33, wherein the primary shaft and the guidewire tube are formed from stainless steel and are attached via welding.

* * * * *